(12) United States Patent
Cerovic et al.

(10) Patent No.: US 8,257,982 B2
(45) Date of Patent: Sep. 4, 2012

(54) METHOD AND DEVICE FOR CHARACTERIZING BIOLOGICAL TISSUE

(75) Inventors: Zoran Cerovic, Paris (FR); Nicolae Moise, Gif sur Yvette (FR); Yves Goulas, Le Plessis Robinson (FR); Jean-Luc Ayral, Antony (FR)

(73) Assignees: FORCE-A, Orsay (FR); Centre National de la Recherche Scientifique, Paris (FR); Universite Paris Sud, Orsay (FR)

( * ) Notice: Subject to any disclaimer, the term of this patent is extended or adjusted under 35 U.S.C. 154(b) by 357 days.

(21) Appl. No.: 12/599,871

(22) PCT Filed: May 7, 2008

(86) PCT No.: PCT/FR2008/050809
§ 371 (c)(1),
(2), (4) Date: Nov. 12, 2009

(87) PCT Pub. No.: WO2008/152267
PCT Pub. Date: Dec. 18, 2008

(65) Prior Publication Data
US 2010/0279332 A1 Nov. 4, 2010

(30) Foreign Application Priority Data

May 11, 2007 (FR) ..................................... 07 03436

(51) Int. Cl.
*G01N 21/76* (2006.01)
*G01N 21/00* (2006.01)
*G01C 3/12* (2006.01)
(52) U.S. Cl. ........................... 436/172; 356/17; 356/434
(58) Field of Classification Search .................. None
See application file for complete search history.

(56) References Cited

U.S. PATENT DOCUMENTS 6,071,748 A * 6/2000 Modlin et al. ................ 436/174
2004/0233448 A1 11/2004 Goulas et al.

OTHER PUBLICATIONS

Demotes-Mainard et al. Indicators of Nitrogen Status for Ornamental Woody Plants Based on Optical Measurements of Leaf Epidermal Polyphenol and Chlorophyll Contents; Scientia Horticulturae, vol. 115 (Feb. 21, 2008) pp. 377-385.*

Gitelson et al. Three-Band Model for Noninvasive Estimation of Chlorophyll Carotenoids and Anthocyanin Contents in Higher Plant Leaves; Geophysical Research Letters, vol. 33, L11402 (2006) pp. 1-5.*

Meyer S et al., "Relationships Between Optically Assessed Polyphenols and Chlorophyll Contents and Leaf Mass Per Area Ratio in Woody Plants: A Signature of the Carbon-Nitrogen Balance within Leaves?", Plant, Cell and Environment, Jul. 2006, pp. 1338-1348, vol. 29, No. 7, XP002459287.

Peng S et al., "Adjustment for Specific Leaf Weight Improves Chlorophyll Meter's Estimate of Rice Leaf Nitrogen Concentration", Agronomy Journal, 1993, pp. 987-990, vol. 85, Madison, WI, USA, XP001154895.

Markwell J et al., Calibration of the Minolta SPAD-502 Leaf Chlorophyll Meter, Photosynthesis Reseach, 1995, pp. 467-472, XP009092421.

Goulas Y et al., "Dualex: A New Instrument for Field Measurements of Epidermal Ultraviolet Absorbance by Chlorophyll Fluorescence", Applied Optics, Aug. 10, 2004, pp. 4488-4496, XP002459288.

Cartelat A et al., "Optically Assessed Contents of Leaf Polyphenolics and Chlorophyll as Indicators of Nitrogen Deficiency in Wheat (*Triticum Aestivum L.*)", Field Crops Research, Jan. 14, 2005, pp. 35-49, Elsevier, Amsterdam, NL, XP004699781.

French Search Report from corresponding FR 0703436 dated Nov. 20, 2007.

* cited by examiner

*Primary Examiner* — Rebecca Prouty
*Assistant Examiner* — Paul Martin
(74) *Attorney, Agent, or Firm* — Young & Thompson (57) ABSTRACT

A method and a system for jointly determining the content of a first chromophorous and fluorescent compound and a second chromophorous compound in a biological tissue (30). The determination of the content of the chromophorous and fluorescent compound (33) is carried out by optical measurement of the differential absorption of this chromophorous and fluorescent compound (33) and the determination of the content of the second chromophorous compound (34) is carried out by optical measurement of the fluorescence of the chromophorous and fluorescent compound (33). Optical radiations (11-14) are utilized which are suitably chosen in combination with at least one operation of filtering these radiations suited to using single detection (21) and measurement element for the two determinations.

12 Claims, 8 Drawing Sheets

METHOD AND DEVICE FOR CHARACTERIZING BIOLOGICAL TISSUE

CROSS REFERENCE TO RELATED APPLICATIONS

This Application is a National Stage of PCT/FR2008/050809, filed May 7, 2008, which claims priority of FRANCE 0703436 filed May 11, 2007.

BACKGROUND OF THE INVENTION

The present invention relates to a method for characterizing a biological tissue. It also relates to a system implementing this method.

Field of the Invention

The invention relates, more particularly, to a method and a system for characterizing a biological tissue, such as a plant leaf, comprising a first chromophorous and fluorescent compound, such as chlorophyll, and a second chromophorous compound which is slightly or not at all fluorescent, such as a flavonoid. The characterization aims to determine the content of a chromophorous and fluorescent compound and a second chromophorous compound in the biological tissue. Such a characterization of a biological tissue is very useful as the content of a chromophorous and fluorescent compound and a second chromophorous compound in the biological tissue represents information concerning the constitution and the biological state of the concerned tissue and facilitates the management and treatment of the entity from which the biological tissue originates.

Discussion of the Prior Art

The document FR 2 830 325 discloses an optical instrument which makes it possible to measure light absorption characteristics of a sample of biological tissue comprising a chromophorous and fluorescent compound and a second chromophorous compound which is only slightly or not at all fluorescent. The method disclosed in this document involves measuring the fluorescence induced by excitation of the fluorescent compound by a first and a second radiation of different wavelengths illuminating the biological tissue sample. One of these so-called reference radiations is slightly or not at all absorbed by the second compound whereas the other is relatively well absorbed. By measuring the fluorescence induced by the two radiations and finding the ratio of the measured fluorescences, the method makes it possible to measure the light absorption characteristics of the sample and as a result the content of the second compound in the biological tissue.

The state of the art also comprises the optical measurement of the content of a chromophorous and fluorescent compound in a biological tissue by a differential absorption measurement of this compound, as described in the document U.S. Pat. No. 4,986,665. In general such a measurement utilizes two light sources: one situated in an absorption band of this compound and another which is situated outside this absorption band.

However, at present no system exists for jointly measuring the content of a chromophorous and fluorescent compound and a second chromophorous compound, which is slightly or not at all fluorescent, in a biological tissue by the measurement methods described above.

SUMMARY OF THE INVENTION

A purpose of the invention is to propose a method and a system for the joint measurement of the content of a chromophorous and fluorescent compound and a second chromophorous compound in a biological tissue by the measurement methods described above.

DETAILED DESCRIPTION OF THE INVENTION

The invention thus proposes a method for characterizing a sample of biological tissue comprising a first chromophorous and fluorescent compound and a second chromophorous compound, said process comprising the following steps:
  determination, by optical measurement of the absorption characteristics of the biological tissue, and more particularly of the chromophorous and fluorescent compound, of the content of this chromophorous and fluorescent compound in the sample;
  determination, by optical measurement of fluorescence of the chromophorous and fluorescent compound, of the content of the second chromophorous compound in said sample.

The term "second chromophorous compound" denotes a chromophorous compound which is slightly or not at all fluorescent.

The term "biological tissue" denotes a tissue originating from a living entity, such as a plant, human being or animal. One example of biological tissue is a plant leaf.

The determination of the content of the second chromophorous compound is well known to a person skilled in the art, and need not be described in detail here. For more details on this subject, reference may be made to the document FR 2 830 325 the teaching of which is included in the present application. Similarly, the determination of the content of the chromophorous and fluorescent compound is carried out by the measurement of differential absorption, which is also well known to a person skilled in the art, and also need not be described in detail here. For more details on this subject, reference may be made to the document U.S. Pat. No. 4,986,665.

It is not obvious for a person skilled in the art to carry out the joint determination of the content of a chromophorous and fluorescent compound and a second chromophorous compound in a biological tissue as these two determinations, involving the measurement both of the absorption and of the fluorescence of the same chromophorous and fluorescent compound, are considered as being incompatible. In fact, the currently known methods carry out these determinations separately as they utilize measurements involving light sources the wavelengths of which are not compatible with each other. This leads a person skilled in the art to think that these two determinations cannot be carried out jointly.

Advantageously, the method according to the invention makes it possible to carry out these two determinations jointly, which has a certain usefulness for the characterization of the biological tissue and for the management of the entity from which this biological tissue originates. Moreover, a joint determination of the content of a chromophorous and fluorescent compound and a second chromophorous compound in a biological tissue makes it possible to achieve a gain in time and precision compared with the methods of the state of the art.

Moreover, the method according to the invention advantageously makes it possible to characterize the biological tissue non-destructively and in situ.

The method according to the invention can moreover comprise a step of determination of a quantity proportional to the ratio of the content of the chromophorous and fluorescent compound to the content of the second chromophorous compound. In the application example which is in no way limitative, where the biological tissue is a plant leaf comprising a chromophorous and fluorescent compound which is chlorophyll and a second chromophorous compound which is a compound of the family of the phenylpropanoids or the polyphenols, such as a flavonoid, the method according to the invention makes it possible to determine a quantity proportional to the ratio of the content of chlorophyll to the content of flavonoid in the plant leaf. Studies show that the chlorophyll/flavonoid ratio is characterized by zones of stability along a plant leaf and a more precise capacity to distinguish the nitrogen requirement. This makes it an important indicator for crop management. See on this subject the article by Aurélie Cartelat et al. entitled "*Optically assessed contents of leaf polyphenolics and chlorophyll as indicators of nitrogen deficiency in wheat* (Triticum aestivum L.)". (Field Crops Research, 2005, 91: p. 35-49).

According to an embodiment of the method according to the invention, the determination of the content of the second chromophorous compound in the sample can comprise the following operations:
  emission, by first means of emission in the direction of the sample, of a first and of a second optical radiation, of different wavelengths, each chosen so as to induce a radiation of fluorescence of the chromophorous and fluorescent compound,
  a first measurement, by first measurement means, of the radiations of fluorescence induced by the first and second radiations, and
  determination, from the first measurement, of the content of the second chromophorous compound in the sample.

Similarly, the determination of the content of the chromophorous and fluorescent compound in the sample can comprise the following operations:
  emission, by second means of emission in the direction of the sample, of a third and fourth optical radiation, of different wavelengths, each intended to be partially absorbed by the chromophorous and fluorescent compound, but in different quantities,
  a second measurement, by second measurement means, of at least one unabsorbed part of the third and fourth radiations, and
  determination, from the second measurement, of the content of the chromophorous and fluorescent compound in the sample.

By unabsorbed part of the third and fourth radiations is meant the part of the third and fourth radiations which is reflected or transmitted by the chromophorous and fluorescent compound.

The first measurement can comprise at least one measurement on the side of the first emission means. In this case the first measurement means are situated at least partly on the side of the first emission means. The fluorescent radiations measured are the radiations of fluorescence which propagate towards the first emission means.

The first measurement can comprise at least one measurement on the side opposite to the first emission means, in this case the first measurement means are situated at least partly on the side opposite to the first emission means. The fluorescent radiations measured are the radiations of fluorescence which propagate towards the side opposite to the first emission means.

Moreover, the second measurement can comprise at least one measurement on the side of the second emission means. In this case the second measurement means are situated at least partly on the side of the second emission means and carry out the measurement of the part of the third and fourth radiations not absorbed by the chromophorous and fluorescent compound, which propagate towards the second emission means, i.e. the part of the third and fourth radiations reflected by the chromophorous and fluorescent compound.

The second measurement can also comprise at least one measurement on the side opposite to the second emission means. In this case the second measurement means are situated at least partly on the side opposite to the second emission means and carry out the measurement of the unabsorbed part of the third and fourth radiations which propagate towards the side opposite to the second emission means, i.e. the part of the third and fourth radiations transmitted by the chromophorous and fluorescent compound.

Moreover, the first measurement means and the second measurement means can comprise shared detection means, the method also comprising at least one first filtering, between the sample and the detection means, the first filtering being intended to:
  block, at least partly, the first and second radiations from passing through towards the detection means, and
  allow, at least partly, the part of the third and fourth radiations not absorbed by the sample to pass through, which propagates towards the detection means.

In fact, the method according to the invention can comprise the utilization of single detection means, i.e., used both for the measurement of the radiations of fluorescence of the chromophorous and fluorescent compound and for the measurement of the part of the third and fourth radiations not absorbed by this same compound. The use of single detection means poses problems of incompatibility of the wavelengths involved during these measurements, i.e. during the measurement, on the one hand, of the content of the second chromophorous compound in the biological tissue by the method of fluorescence of the chromophorous and fluorescent compound, and on the other hand of the content of the chromophorous and fluorescent compound by differential absorption of the chromophorous and fluorescent compound. The method according to the invention makes it possible to solve this problem by the first filtering carried out between the sample and the single detection means.

The use of single filtering means for the two measurements is advantageously less expensive to implement, requires less space and satisfies the constraints linked to the optical coupling between the measured surface of the biological tissue and the detection means when the detection means for the two measurements are separate.

The advantage of single detection and filtering means also becomes apparent when these detection means are image acquisition means such as a CCD camera. In this case, it is ensured that it is possible to establish a pixel to pixel correspondence between the images produced by the first, second, third and fourth radiations.

According to an advantageous version of the method according to the invention, in addition to the single detection means, single measurement means can be utilized for the joint measurement of the radiations of fluorescence of the chromophorous and fluorescent compound and of the radiations originating from the second emission means, which are not absorbed by this same compound.

Moreover, the method according to the invention can advantageously comprise, between the emission means and the sample, a second filtering provided in order to block at least part of the radiations emitted in the direction of the sample. This filtering operation can involve eliminating an undesirable part of the radiations emitted towards the sample by the first and the second emission means.

According to the invention, the first radiation is chosen such that its wavelength:
1. is not comprised within an absorption wavelength band of the second chromophorous compound, and
2. is comprised within an excitation wavelength band of the fluorescence of the chromophorous and fluorescent compound;

and the second radiation is chosen such that its wavelength:
3. is comprised within an absorption wavelength band of the second chromophorous compound, and
4. is comprised within an excitation wavelength band of the fluorescence of the chromophorous and fluorescent compound.

Similarly, the third radiation is chosen such that its wavelength:
1. is comprised within an absorption wavelength band of the chromophorous and fluorescent compound, and
2. is not comprised within an absorption wavelength band of the second chromophorous compound;

and the fourth radiation is chosen such that its wavelength:
3. is not comprised within an absorption wavelength band of the chromophorous and fluorescent compound, and
4. is not comprised within an absorption wavelength band of the second chromophorous compound.

Advantageously, the second (or the first) optical radiation can be emitted at a predetermined intensity and the first (the second) optical radiation is emitted at a variable intensity so that the radiations of fluorescence induced by each of the first and second radiations are equal in intensity. The intensity of the first (the second) radiation is then adjusted as a function of a so-called control signal, in relation to the intensities of the radiations of fluorescence induced on the one hand by the first radiation and on the other hand by the second radiation. The method according to the invention thus makes it possible to control the effects of variable fluorescence of the chromophorous and fluorescent compound, for the purpose of carrying out a more rapid and more precise determination of the content of the second chromophorous compound in the biological tissue.

Moreover, the intensities of the first and of the second radiation can vary alternately, with a phase shift, at a predetermined frequency, as well as the intensities of the third and of the fourth radiation, thus allowing an individual measurement:
of each of the radiations of fluorescence induced by each of the first and second radiations, and
of the part of each of the third and fourth radiations not absorbed by the biological tissue.

According to an advantageous characteristic of the method according to the invention, the determination of the content of the chromophorous and fluorescent compound and the determination of the content of the second chromophorous compound content are carried out alternately.

Moreover, each of the radiations can be emitted in the form of pulses. For example, during the determination of the content of the second chromophorous compound in the tissue, pulses of the first and of the second radiation can be emitted alternately at a predetermined frequency.

Moreover, the intensities of the first, second, third and fourth radiations can vary periodically, such as for example a sinusoidal or quasi-sinusoidal modulation, and at different modulation frequencies, thus allowing an individual measurement:
of each of the radiations of fluorescence induced by each of the first and second radiations, and
of the part of each of the third and fourth radiations not absorbed by the biological tissue.

According to another aspect of the invention, a use of the method according to the invention for the characterization of a plant leaf is proposed, where the chromophorous and fluorescent compound is chlorophyll and the second chromophorous compound comprises a compound of the family of the phenylpropanoids, in particular the flavonoids. The radiations used can have wavelengths chosen around the following values:
the first radiation: 650 nm;
the second radiation: 370 nm;
the third radiation: 720 nm; and
the fourth radiation: 780 nm.

Advantageously, the use according to the invention can also comprise a determination of the carbon allocation regulation under the influence of the availability of nitrogen as a function of the content of chlorophyll and phenylpropanoids. See on this subject the article by Sylvie Meyer et al. entitled "Relationships between optically assessed polyphenols and chlorophyll contents, and leaf mass per area ratio in woody plants: a signature of the carbon-nitrogen balance within leaves?" (Plant, Cell and Environment, 2006, 29: p. 1338-1348).

Other uses can be envisaged such as the characterization of the efficiency of excitation energy transfer by the carotenoids in the leaves to the chlorophyll. In this case the carotenoids play the role of the second non-fluorescent chromophorous compound.

According to a third aspect of the invention, a system for characterizing a sample of biological tissue is proposed, comprising a first chromophorous and fluorescent compound and a second chromophorous compound, said system comprising:
first means for determining, by optical measurement of fluorescence of the chromophorous and fluorescent compound, the content of the second chromophorous compound in the sample;
second means for determining, by optical measurement of the absorption characteristics of the chromophorous and fluorescent compound, the content of the chromophorous and fluorescent compound in the sample.

The system according to the invention can moreover comprise calculation means for determining a quantity proportional to the ratio of the content of the chromophorous and fluorescent compound to the content of the second chromophorous compound. These calculation means can comprise programmes intended to be used in electronic or computing means.

According to a particular embodiment of the system according to the invention, the first means can comprise:
first means of emission in the direction of the sample of a first and a second optical radiation, of different wavelengths, each chosen so as to induce a radiation of fluorescence of the chromophorous and fluorescent compound,
first measurement means, for measuring the radiations of fluorescence induced by the first and second radiations,
calculation means for determining, from the measurement of the radiations of fluorescence, the content of the second chromophorous compound in the sample; and
the second means can comprise:
second means of emission in the direction of the sample, of third and fourth optical radiations, of different wavelengths, each intended to be partially absorbed, but in different quantities, by the chromophorous and fluorescent compound, second measurement means, for measuring at least one unabsorbed part of the third and fourth radiations, and calculation means for determining, from the measurement of at least one unabsorbed part of the third and fourth radiations, the content of the chromophorous and fluorescent compound in the sample.

In an advantageous version of this embodiment, the first measurement means and the second measurement means comprise shared detection means, the system also comprising first filtering means, arranged between the sample and the detection means, the first filtering means being intended to:

block, at least partly, the first and second radiations from passing through towards the measurement means, and allow, at least partly, the part of the third and fourth radiations not absorbed by the sample to pass through and propagate towards the detection means.

The detection means can in particular comprise a silicon photodiode provided for detecting on the one hand the radiations of fluorescence of the chromophorous and fluorescent compound induced by each of the first and second radiations, and on the other hand the unabsorbed part of the third and fourth radiations. Moreover, the first filtering means can comprise at least one coloured filter.

According to a first embodiment of the system according to the invention, the detection means are arranged on one side of the tissue sample and the first and second emission means are arranged on the other side of the sample. In this embodiment, the detection means detect:

the radiations of fluorescence which propagate towards the side opposite to the first and second emission means, and the unabsorbed part of the third and fourth radiations which propagate towards the side opposite to the first and second emission means, i.e. the part of the third and fourth radiations transmitted by the chromophorous and fluorescent compound.

In this first embodiment, the system according to the invention can be presented in the form, for example, of tongs.

According to a second embodiment of the system according to the invention, the detection means, and the first and the second emission means are arranged on the same side of the tissue sample. In this embodiment, the detection means detect:

the fluorescent radiations of the chromophorous and fluorescent compound which propagate towards the first and the second emission means, and the part of the third and fourth radiations not absorbed by the chromophorous and fluorescent compound which propagate towards the first and the second emission means, i.e. the part of the third and fourth radiations reflected by the chromophorous and fluorescent compound.

Advantageously, the system according to the invention can moreover comprise means for the amplification and/or analysis of the radiations detected by the detection means.

Moreover, the system according to the invention can also comprise second filtering means, arranged between the emission means and the sample, and provided for blocking at least one undesirable part of the radiations emitted in the direction of the sample.

The system can also comprise command and control means supplying a control signal to the first emission means so that the radiations of fluorescence induced by the first and the second optical radiation are substantially equal in intensity.

Moreover, the system can advantageously comprise synchronization means supplying a synchronization signal to the first and second emission means so that:

the intensities of the first and second radiation vary periodically, as regards phase shift in relation to each other, and the intensities of the third and of the fourth radiation vary periodically, as regards phase shift in relation to each other.

On the other hand, the system can alternatively comprise modulation means supplying a modulation signal towards the emission means so that the intensities of the first, second, third and fourth radiations vary periodically, for example sinusoidally, at different modulation frequencies.

BRIEF DESCRIPTION OF THE DRAWINGS

Other characteristics and advantages of the invention will become apparent on examination of the detailed description of an embodiment which is in no way limitative, and the attached drawings in which.

The non-limitative embodiment example that we describe below relates to a system for the joint measurement the content of chlorophyll, a chromophorous and fluorescent compound, and of polyphenols, a second chromophorous compound in a plant leaf. The measurement of the polyphenols is carried out by the chlorophyll fluorescence method described in the document FR 2 830 325. The measurement of the chlorophyll is carried out by measuring the differential absorption of the chlorophyll.

Figure 1:
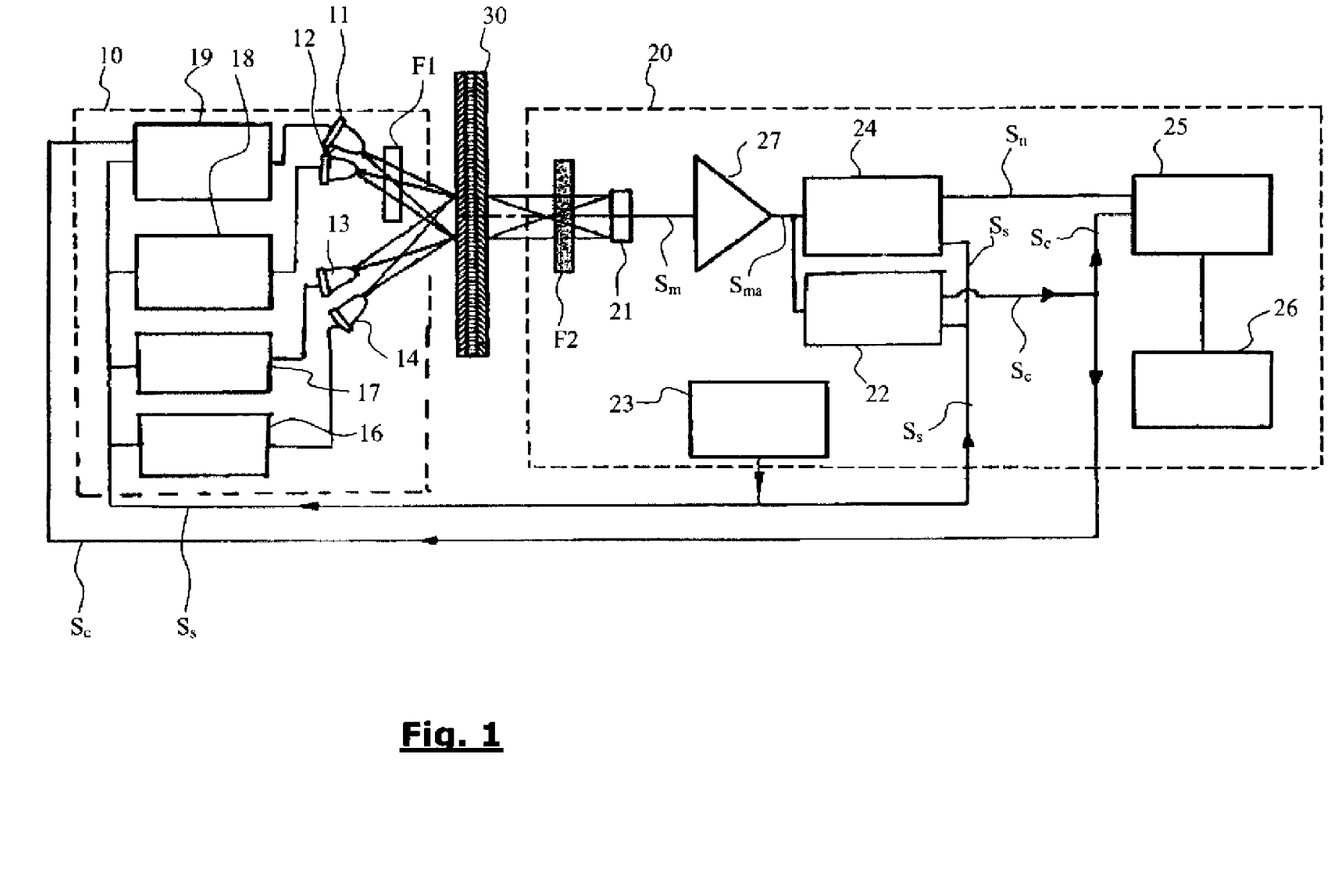
FIG. 1 is a diagrammatic representation of a first embodiment of the system according to the invention.

FIGS. 1 and 1 bis show two embodiments of such a system of joint measurement of the content of chlorophyll and polyphenols in a plant leaf. In these two embodiments, the system is presented in the form of two parts: an emitting part 10 and a receiving part 20. In the first embodiment represented in FIG. 1, the emitting 10 and receiving parts 20 are arranged on either side of the plant leaf sample 30, whereas in the second embodiment represented in FIG. 1bis, the emitting 10 and receiving 20 parts are arranged on the same side of the plant leaf sample 30.

Figure 1B:
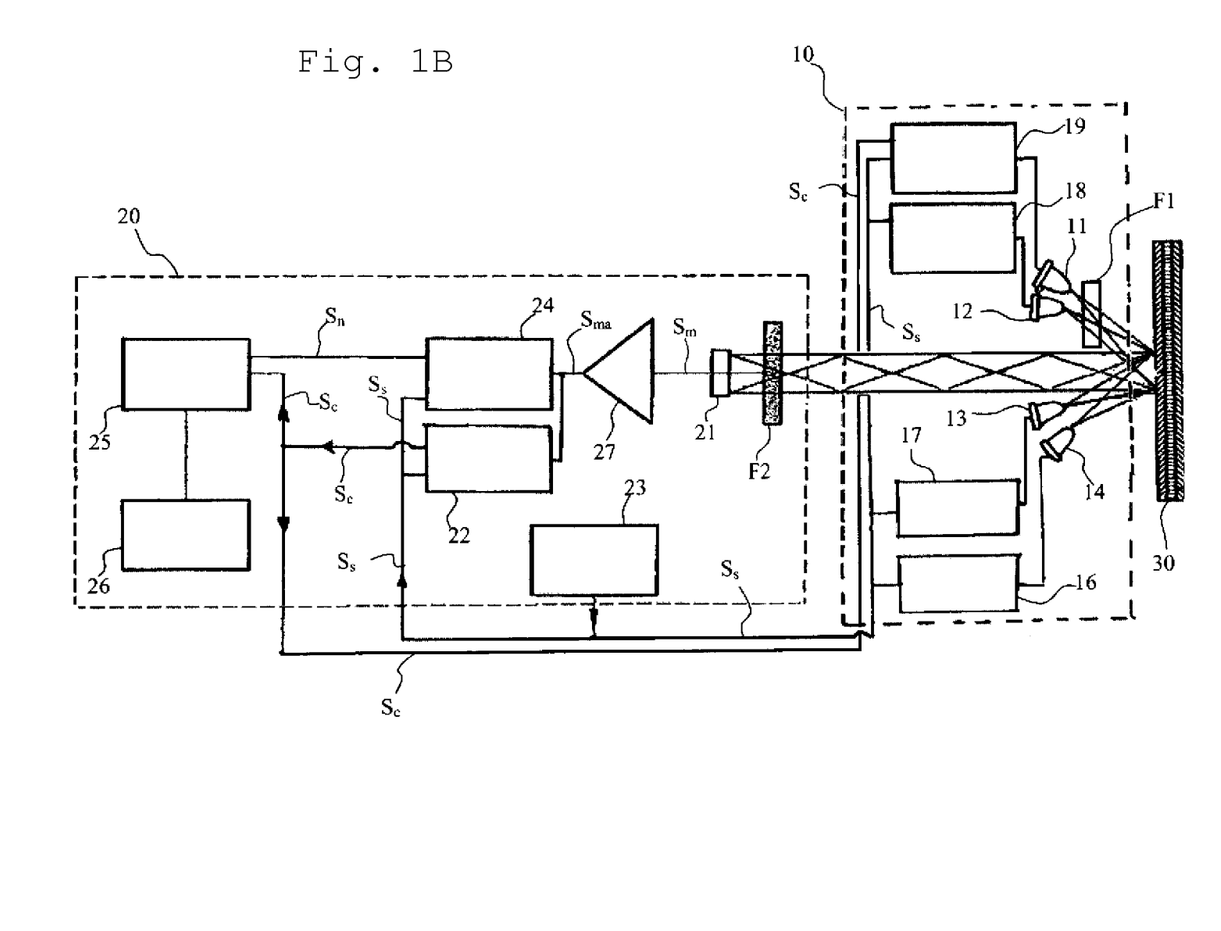
FIG. 1B is a diagrammatic representation of a second embodiment of the system according to the invention.

Whatever the embodiment, the emitting part 10 comprises four radiation sources 11, 12, 13, 14 illuminating the front surface of a plant leaf sample 30. Each of these sources 11-14 is associated with a pulsed supply 16-19, as shown in FIGS. 1 and 1B, and controlled by a synchronization signal Ss. The sources 11, 12 serve to measure the content of polyphenols in the leaf 30 and are provided to induce the fluorescence of chlorophyll. The other two sources 13, 14 serve to measure the absorption due to the chlorophyll and therefore the determination of the chlorophyll content in the sample 30. The emitting part 10 also comprises an optical filter F1 situated between the sources 11 and 12 and the sample 30.

The receiving part 20 of the system according to the invention comprises a detector 21, preferentially a silicon photodiode supplying an electrical signal as a function of the radiations detected, associated with an optical filter F2, arranged between the sample 30 and the detector 21. The function of this filter F2 is to:

block the radiations from the excitation sources of 11 and 12 from passing through towards the detector 21, partially or totally transmit the part of the radiations from the other two sources 13 and 14 not absorbed by the chlorophyll, and also partially or totally transmit the emission of the fluorescence of the chlorophyll induced by the optical radiations emitted by the sources 11 and 12.

The filter F1 is provided in order to improve the spectral purity of the radiations emitted by the sources 11 and 12 and to block any radiation originating from these sources which would correspond to the sensitivity band of the filter F2.

The receiving part 20 of the system also comprises a command and control unit 22 and a unit 23 for synchronizing the supplies 16-19 and therefore the sources 11-14. The system also comprises in the receiving part a measurement and conversion unit 24, a calculation unit 25 comprising calculation means connected to one or more peripherals 26 comprising storage means, data transmission means, as well as a user interface such as a screen and a keyboard. Finally, the receiving part 20 of the system according to the invention comprises means for amplification 27 of the electrical signal supplied by the detector 21.

The sources 12, 13, 14 have a fixed intensity, which is pre-programmed or can be adjusted by the user. The intensity of the source 11 is variable and is under the control of the control unit 22. The control unit 22 acts on the supply 19 via a control signal Sc in order to adjust the intensity of the source 11 such that the fluorescence of the chlorophyll induced by this source 11 is equal to the fluorescence of the chlorophyll induced by the source 12. Start of the sources 11-14 is controlled by a synchronization unit 23, comprising electronic synchronization means, acting on the supplies 16-19 via the synchronization signal Ss.

Figure 2:
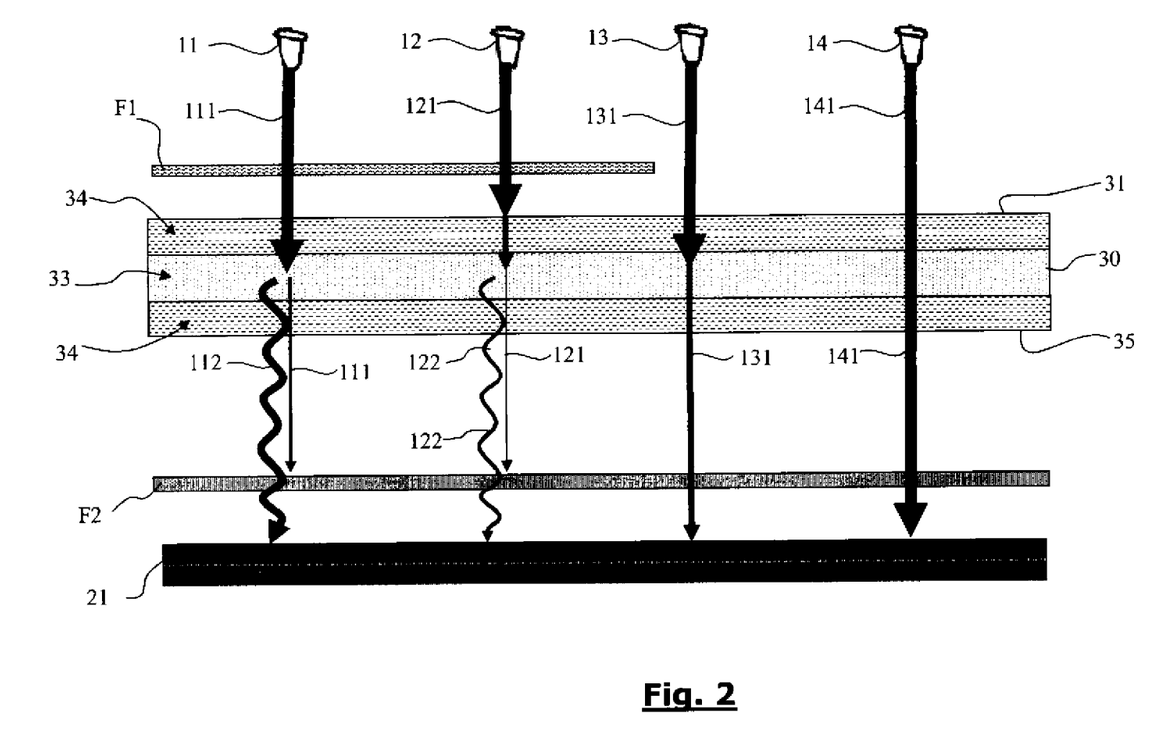
FIG. 2 is a diagrammatic representation of the measurement principle, in the first embodiment of the system according to the invention.
Figure 2B:
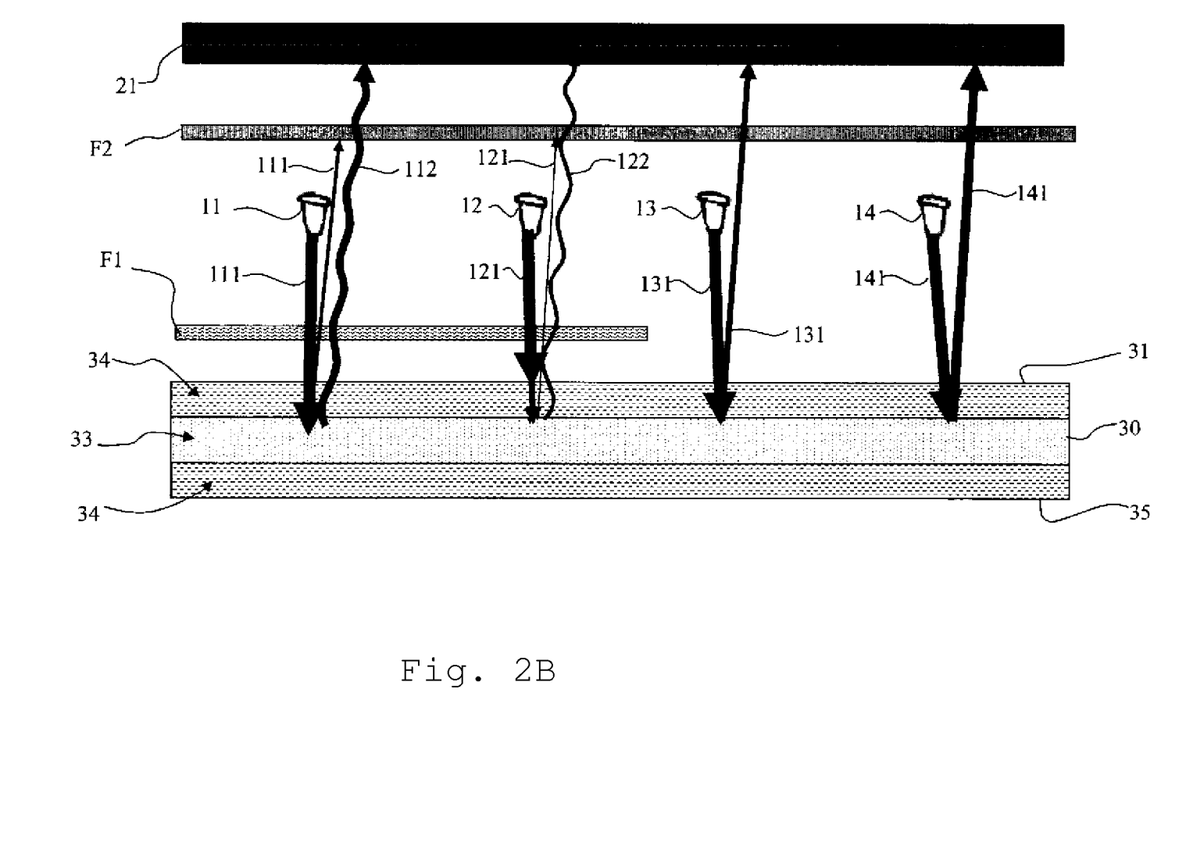
FIG. 2B is a diagrammatic representation of the measurement principle, in the second embodiment of the system according to the invention.

FIGS. 2 and 2B are diagrammatic representations of the measurement principle and of the optical paths of the different radiations, in the first and the second embodiment respectively. With reference to FIGS. 2 and 2bis, the four sources 11-14, are preferentially light-emitting diodes (LEDs) and illuminate the same surface 31 of the leaf 30. The sources 11 and 12 are provided to emit two radiations, 111 and 121 respectively, intended to induce the fluorescence of the chlorophyll 33 and to induce two fluorescent radiations, 112 and 122 respectively. The other two sources 13, 14 are provided to emit two radiations, 131 and 141 respectively, intended to be partially absorbed, but in different quantities, by the leaf 30, and more precisely by the chlorophyll 33.

FIG. 2 represents:

the fluorescent radiations 112 and 122 emitted by the chlorophyll towards the side opposite to the sources 11 and 12, and the transmitted part of the radiations 131 and 141.

In the first embodiment the receiving part 20 of the system being situated on the side of the leaf opposite to the emitting part 10, it is the radiations emitted towards the side opposite to the sources 11-14 which are detected by the detector 21. In fact, in this first embodiment, the detector 21 is provided in order to detect, on the one hand the fluorescence emitted towards the rear surface 35 of the leaf in order to measure the polyphenols content 34, and also detect the transmittance of the leaf 30 which makes it possible to determine the chlorophyll content 33.

FIG. 2bisbisrepresents:

the fluorescent radiations 112 and 122, induced by the radiations 111 and 121, and emitted by the chlorophyll towards the sources 11 and 12, and the reflected part of the radiations 131 and 141.

In the second embodiment, as the receiving part 20 of the system is situated on the same side of the leaf as the emitting part 10, it is the radiations emitted towards the sources which are detected by the detector 21. In fact, in this second embodiment, the detector 21 is provided to detect, on the one hand the fluorescence emitted towards the front surface 31 of the leaf in order to measure the content of polyphenols 34 and, on the other hand, the part of the radiations 131 and 141 reflected by the leaf (30) in order to measure the reflectance of the leaf 30 which makes it possible to determine the content of chlorophyll 33.

The first and the second embodiment are substantially equivalent because, in a biological tissue, reflectance and transmittance are correlated.

Whatever the embodiment, the wavelengths of each of the sources 11-14 are chosen as a function of the absorption bands of the compounds to be measured, their technical characteristics such as spectral purity or their power, their commercial availability and cost, and the commercial availability and cost of the filter or filters F2 associated with the detector 21.

For the joint measurement of the polyphenols 34 and chlorophyll 33 in the leaf 30, the detector 21 is a silicon photodiode. The filter F2 is a 3 mm RG715 coloured filter from Schott (Germany). The spectral transmission band of such a filter is 720 nm (mid-height, 45% transmission) at 900 nm and beyond.

The source 11 emits a radiation 111 in the red range, where the polyphenols 34 do not absorb, which induces the fluorescence of the chlorophyll 33 and causes the emission of a radiation of fluorescence 112, and which serves as a reference for the measurement of the absorption by the polyphenols 34. The wavelength of this source is preferentially 650 nm, which makes it possible to avoid absorption by the anthocyanins, and constitutes an isosbestic point of the absorption spectra of the chlorophylls a and b. The source 12 is a source emitting a radiation 121 in the ultraviolet range, the wavelength of which is situated in an absorption band of the polyphenols 34 and which induces the fluorescence of the chlorophyll 33 and causes the emission of a radiation of fluorescence 122. The wavelength of this source 12 can for example be around 370 nm. Examples of UV sources are the Roithner Lasertechnik NS370L or UVLED370-10 diode.

The sources 11 and 12 successively illuminate the leaf 30 by emission of a radiation 111 and 121 respectively. The ultraviolet radiation 121 is absorbed in a variable quantity by the epidermis of the leaf depending on its content of polyphenols 34, whereas the red radiation 111 is not. These radiations 111 and 121 induce the fluorescence of the chlorophyll 33 which then respectively emits radiations of fluorescence 112 and 122 in the red range and in the near infrared range, the intensities of which are proportional to the intensities of the radiations 111 and 121 received by the chlorophyll 33. The radiations of fluorescence 112 and 122 are emitted on the one hand towards the front surface 31 (FIG. 2B) and on the other hand towards the rear surface 35 (FIG. 2) of the leaf 30. The measurement of the ratio of the fluorescence emissions excited by the source 11 and by the source 12 makes it possible to determine the transmittance of the epidermis, and hence its polyphenols level or content by the relationship:

$$phen = C_0 \log\left(\frac{F_R}{F_{UV}}\right) \quad (1)$$

where phen is the content of polyphenols in the epidermis of the leaf 30 in $i/cm^2$, $C_0$ a constant and $F_R$ and $F_{UV}$ are the intensities of radiations of fluorescence 112 and 122 emitted by the chlorophyll excited by the sources 11 and 12.

The source 13 is a source emitting a radiation 131 at 720 nm, at the limit of the bandwidth of the detection filter F2. This radiation is partly absorbed by the chlorophyll and the unabsorbed part propagates on the one hand towards the front surface 31 of the leaf, as shown in FIG. 2bisbisand on the other hand towards the rear surface 35 of the leaf, as shown in FIG. 2.

The source 14 is a source emitting a radiation 141 at 780 nm or beyond. This radiation 141 is almost not at all or only slightly absorbed by the chlorophyll 33, and the unabsorbed part propagates towards the front surface 31 (FIG. 2bis) and towards the rear surface 35 (FIG. 2) of the leaf 30. The source 14 serves as a reference for the measurement of the content of chlorophyll 33 in the leaf 30. The differential of the intensities of the unabsorbed part of the radiations 131 and 141, respectively at 720 and 780 nm, makes it possible to estimate the chlorophyll content by the relationship:

$$chl = C_2\left[\log\left(\frac{I_{780}}{I_{720}}\right) - C_1\right] \quad (2)$$

where chl is the content of chlorophyll in the leaf 30 in $\mu g/cm^2$, $C_1$ and $C_2$ are constants and $I_{780}$ and $I_{720}$ are respectively the intensities of the part of the radiations 141 and 131 not absorbed by the chlorophyll 33.

Each of the radiations of fluorescence 122 and 112 as well as each of the unabsorbed parts of the radiations 131 and 141, is detected at least partly by the detector 21 which generates an electrical signal $S_m$ which is proportional to the intensity of the radiation detected. This electrical signal $S_m$ is then amplified by the amplification means 27 which supply an amplified electrical signal $S_{ma}$, on the one hand to the measurement and conversion unit 24, and on the other hand to the command and control unit 22. The measurement and conversion unit 24 carries out an analogue-digital conversion of the signal $S_{ma}$ supplying a digital signal $S_n$ to the calculation unit 25.

The command and control unit 22 generates a control signal $S_c$ as a function of the amplified digital signal $S_{ma}$. This control signal $S_c$ is then used to adjust the intensity of the radiation 111 emitted by the source 11. This signal $S_c$ is a function both of the intensities of the radiations of fluorescence 112 and 122 of the chlorophyll induced by the radiations 111 and 121 emitted by the sources 11 and 12 respectively. As described above, this control signal $S_c$ is generated so that the intensities of the radiations of fluorescence 112 and 122 induced by the radiations 111 and 121 are equal.

The control signal $S_c$ is also supplied to the calculation unit 25 which, as a function of the signal $S_n$ and the control signal $S_c$, calculates the content of chlorophyll 33 and polyphenols 34 in the leaf 30.

The synchronization unit 23 makes it possible to synchronize the whole of the system via a synchronization signal $S_s$ supplied to the supplies 16-19, to the measurement and conversion unit 24 and to the command and control unit 22.

The chlorophyll/polyphenols ratio can then be determined by the calculation unit 25. It has been demonstrated that this ratio is characterized by zones of stability along the leaf 30 and is better able to determine the nitrogen requirement of the plant whereas the polyphenols or chlorophyll, taken in isolation, vary both along the leaf and according to the dose of nitrogen supplied. Thus the chlorophyll/polyphenols ratio is an important indicator for crop management.

Other spectral combinations of the sources 11-14, of the filters F1 and F2 and of the detector can be envisaged depending on:

the compound to be measured by fluorescence: an excitation in the blue (450 nm), green (530 nm) or amber yellow (590 nm) range instead of the ultraviolet makes it possible to measure the anthocyanins; and the coloured filter F2: a filter such as the RG695 (Schott, Germany) makes it possible to use a source 13 around 710 nm, or a filter such as the RG9 makes it possible to use a source 13 around 730 nm. In the first case, it may then be preferable to use another wavelength for the source 12 which can then emit around 620 or 630 nm.

Figure 3:
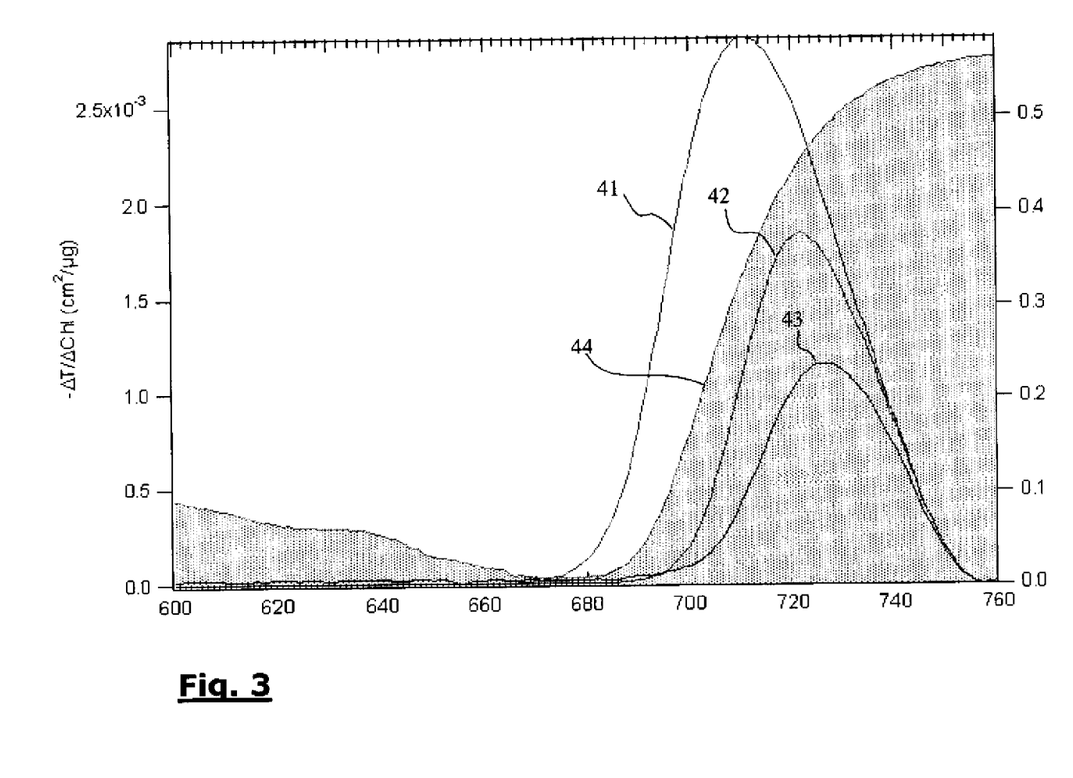
FIG. 3 is a representation of the measurement sensitivities obtained with different components which can be utilized in the system according to the invention.

FIG. 3 shows the $-\Delta T/\Delta Chl$ sensitivity in $cm^2/\mu g$ of measurement of the content of chlorophyll 33 in the leaf 30 as a function of the wavelength, in nm, and of the filter F2 used. The sensitivities are obtained by simulation with the Prospect model, as described by Stéphane Jacquemoud and Frédéric Baret in "*PROSPECT: A Model of Leaf Optical Properties Spectra*", Remote Sens. Environ., 1990. 34: p. 75-91. For an average value of the variation in the chlorophyll content between 40 and 80 $\mu g/cm^2$, the sensitivity 41 obtained with an RG695 type filter F2 and a source 13 at 710 nm is greater than the sensitivity 42 obtained with an RG715 type filter F2 and a source at 720 nm, which is itself greater than the sensitivity 43 with an RG9 type filter F2 and a source 13 at 730 nm. This figure also shows the transmittance band 44 of the leaf 30.

Figure 4:
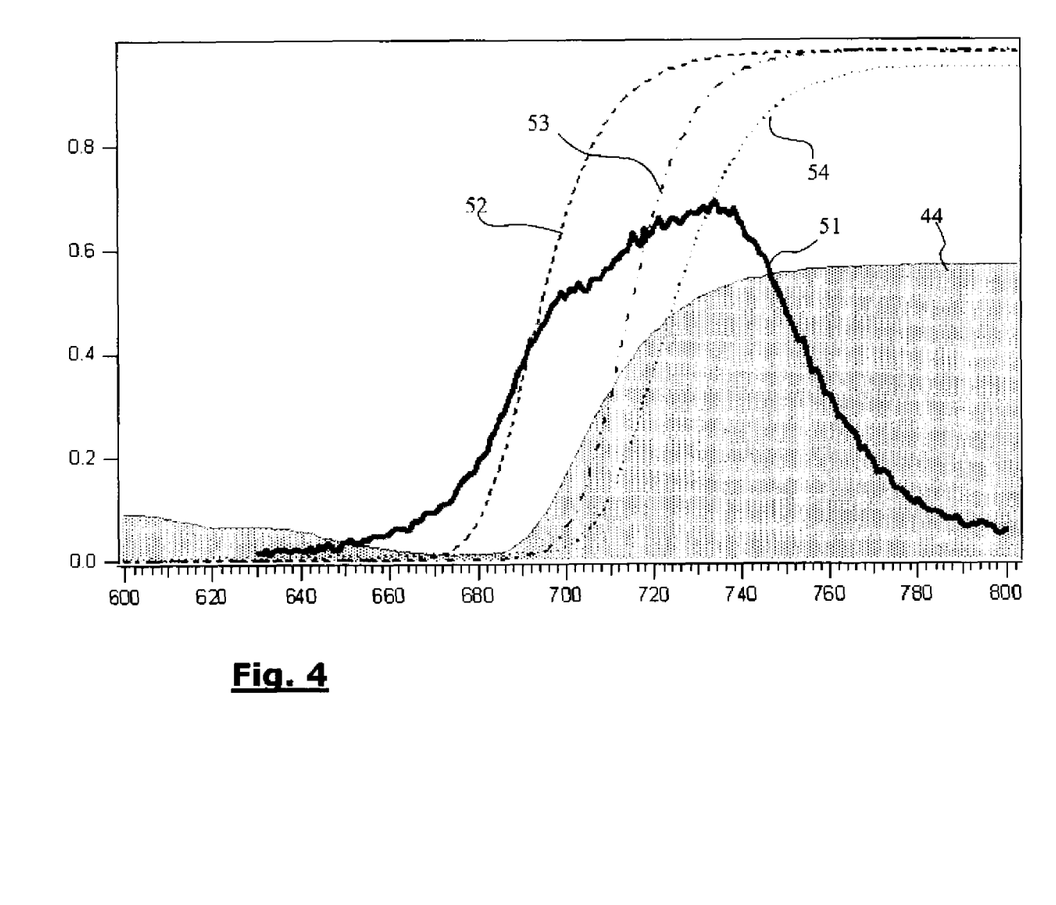
FIGS. 4 and 5 are representations of the fluorescence and transmittance spectra of a plant leaf as well as of the different components which can be utilized in the system according to the invention.
Figure 5:
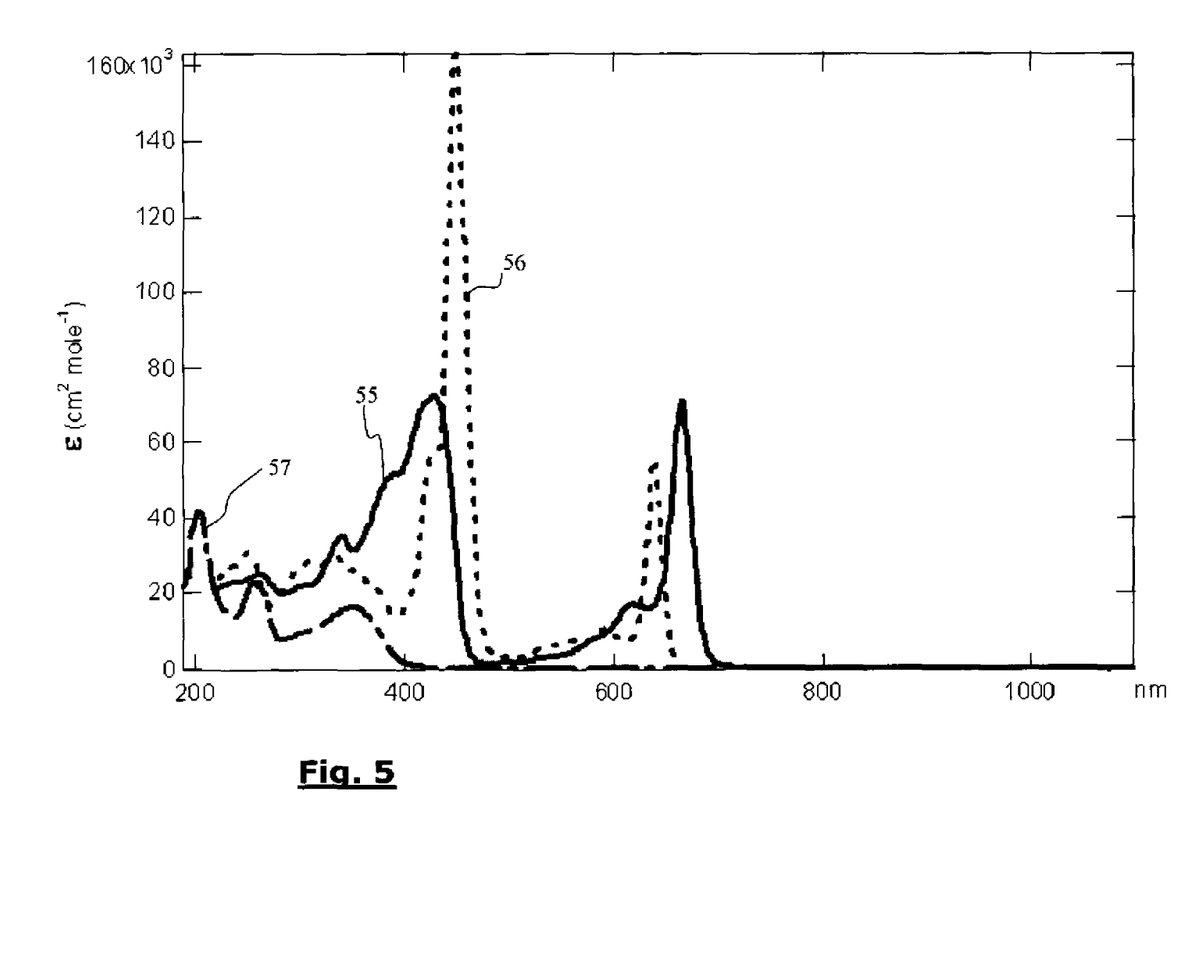

For simpler visualization and comparison of the different wavelengths involved in the examples given above, FIGS. 4 and 5 show the fluorescence band 51 of the rear surface 35 of the leaf 30, the transmittance band 44 of the leaf 30, the spectral band 52 of the RG695 filter, the spectral band 53 of the RG715 filter, the spectral band 54 of the RG9 filter, as well as the absorption bands 55, 56 and 57 respectively of the type a chlorophyll, type b chlorophyll and quercetin which is a polyphenol.

In all the cases described above, the measurements are carried out according to the procedure described hereafter. Firstly, the sources 11 and 12 are activated alternately in order to induce the fluorescence of the chlorophyll. The ratio of the intensities of fluorescence is measured as described in the document FR 2 830 325. The intensity of the source 12 is kept fixed and the intensity of the reference source 11 is adjusted so that the intensities of fluorescence emitted by the leaf are equal. The optical power emitted by the reference source 11 then makes it possible to determine the content of polyphenols in the leaf 30.

Secondly, the sources for measurement of the chlorophyll are activated alternately and the intensities of the parts of the radiations 13 and 14 not absorbed by the leaf are measured. This makes it possible to deduce the chlorophyll content by the relationship (2) above.

It has completely surprisingly been found that, in the first embodiment where the emitting 10 and receiving 20 parts are situated on either side of the biological tissue to be characterized, the system according to the invention can be utilized for the characterization of a thick tissue or of the biological tissue of a thick biological entity by inserting the biological entity directly between the emitting 10 and receiving 20 parts. In this case, the characterization of the biological tissue of an entity can be carried out directly on at least one part of the biological entity without having to take a sample of tissue. The system according to the invention makes it possible, for example, to carry out a characterization of a biological tissue directly on stems, seeds, whole fruits or pieces of fruits. Among the fruits the characterization of which can be carried out by the system according to the invention, there can be mentioned non-limitatively, plums, cherries, olives, berries such as grapes, blackcurrants and gooseberries. Thus, in the first embodiment, the system according to the invention makes it possible to carry out a characterization of a biological tissue in a manner which is more rapid, less complex, and less expensive.

Generally, tests have shown that measurements carried out through a biological tissue from a biological entity, in order to measure:

the content of a chromophorous and fluorescent compound in the tissue,
the content of a chromophorous compound which is only slightly or not at all fluorescent in the tissue, or
both of them can be carried out directly on the entity or on at least a thick part of the entity comprising the tissue. These measurements can also be carried out on thick tissues. Thus, the measurement systems incorporating measurements through the tissue can be used on thick tissues or directly on the entities inserted between the emitting part and the receiving part of these systems. By way of a non-limitative example, the measurements through the tissue described in the brevet FR 2 830 325 can be carried out directly on the biological entity the tissue of which is to be characterized.

Figure 6:
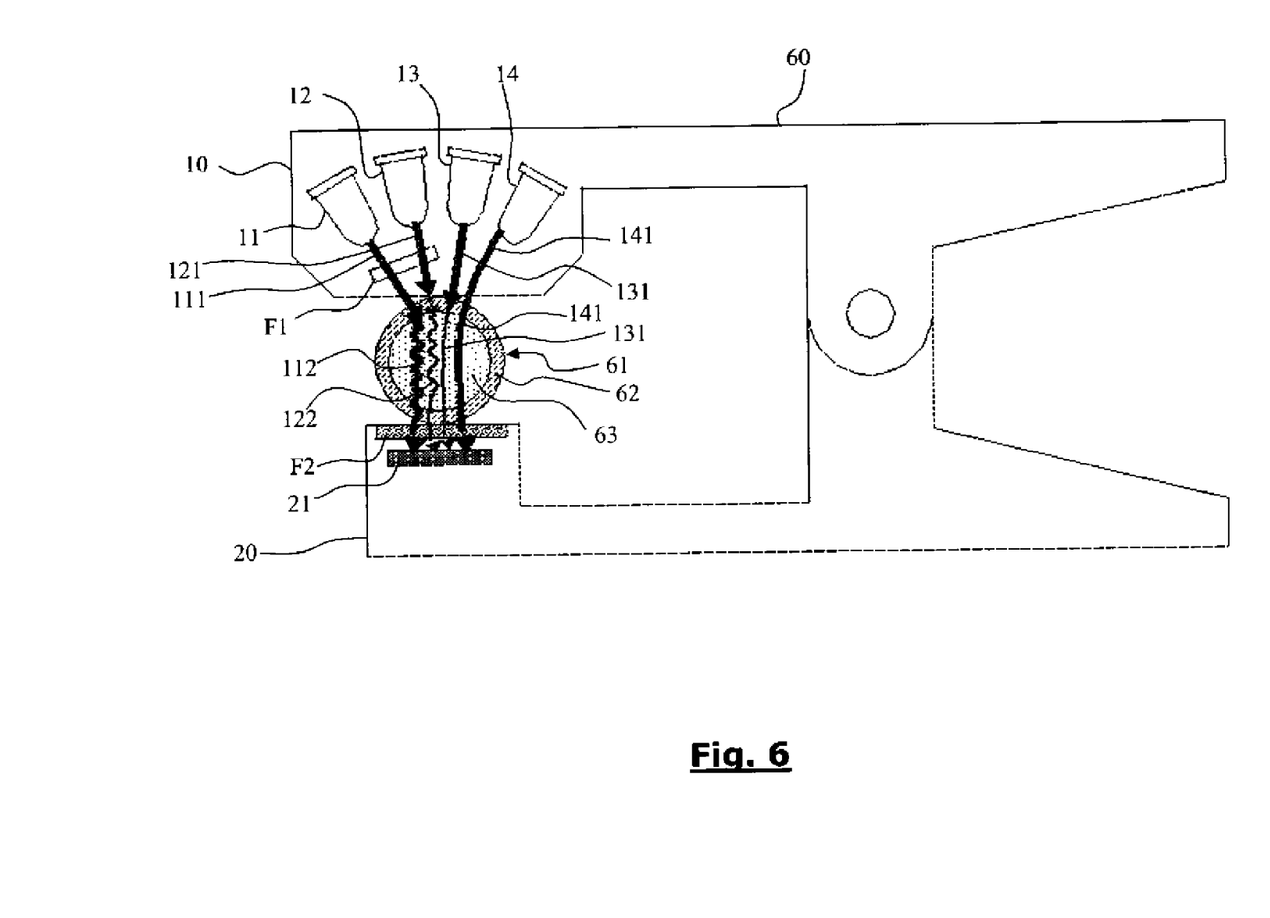
FIG. 6 is a diagrammatic representation of a system according to the invention according to the first embodiment, for the characterization of a grape skin.

In the first embodiment, the system according to the invention can be presented in the form of tongs 60, as represented in FIG. 6, showing on the one hand the emitting part 10 and on the other the receiving part 20. The biological tissue to be characterized, or the biological entity the tissue of which is to be characterized, is inserted directly between the two parts of the tongs. By way of example, FIG. 6 shows the use of the tongs 60 for the characterization of a grape 61. One of the outer surfaces of the grape receives the radiations 111, 121, 131, 141 originating from the sources 11, 12, 13, 14 which are partially absorbed, but in different quantities, by the skin 62 of the grape. The radiations of fluorescence 112 and 122 induced by the radiations 111 and 121, as well as the transmitted part of the radiations 131 and 141 are detected on the opposite outer surface by the detector 21, after passing through the flesh 63. The chromophorous and fluorescent compound measured is the chlorophyll and the second chromophorous compound is either a compound of the family of the phenylpropanoids in a first variant, or a compound of the family of the anthocyanins in a second variant. Thus, the radiations used can have wavelengths chosen around the following values:

the first radiation: 650 nm;
the second radiation: 370 nm for the measurement of a compound of the family of the phenylpropanoids, 530 or 590 nm for the measurement of a compound of the family of the anthocyanins;
the third radiation: 720 nm; and
the fourth radiation: 780 nm.

Of course, the tongs 60 comprise control means, synchronization means or modulation means described above not represented in FIG. 6.

The second embodiment of the system according to the invention can be presented in the form of a device which is portable or mounted on any machine in the precision agriculture and biomedical fields.

Two important, non-limitative, applications of the system according to the invention in this second embodiment can be envisaged:

the contactless or remote estimation of the nitrogen requirement of a crop, with a device which is portable or mounted on a piece of agricultural machinery, for the purpose of guiding farming practices, in particular in precision agriculture,
the in vivo characterization of an animal or human tissue, and in particular the early detection of tumours, the joint measurement of haemoglobin derivatives such as protoporphyrin IX (emission peaks at 630 and 690 nm) as a chromophorous and fluorescent compound and of melanin as a chromophorous compound.

The invention advantageously makes it possible to:

carry out a measurement of the content of a chromophorous and fluorescent compound and a second chromophorous compound in a biological tissue with a single detector for both measurements;
miniaturize the system in order to obtain equipment which is portable, simple to use, stand-alone and low-cost;
use light-emitting diodes as radiation sources;
minimize the space requirement around the measurement point while optimizing the optical coupling by a configuration where the radiation sources are placed on the front surface and the detector on the rear surface of the biological tissue;
optimizing the combination of the wavelengths of the radiation sources and the sensitivity band of the detector in order to carry out a precise and sensitive measurement; and
use a coloured filter which is commonly used in optics arranged between the detector and the biological tissue.

The invention is not limited to the example described in detail above and can be used for characterizing a biological tissue of any type.

The invention claimed is:

1. A method for characterizing a sample of biological tissue (30) comprising a first chromophorous and fluorescent compound (33) and a second chromophorous compound (34), said method comprising the following steps:

determination, by optical measurement of fluorescence of the chromophorous and fluorescent compound (33), of the content of the second chromophorous compound (34) in said sample (30), said determination comprising the following steps:
emission, by first means of emission (11, 12) towards said sample (30), of a first (111) and of a second (121) optical radiation, of different wavelengths, each chosen so as to induce a radiation of fluorescence (112, 122) of said chromophorous and fluorescent compound (33), such that one of the first and second radiations is absorbed by the second chromophorous compound and the other is only slightly or not at all absorbed by the second chromophorous compound,
measurement, by first measurement means, of said radiations of fluorescence (112, 122) induced by said first and second radiations (111, 121), and
determination, from said first measurement, of the content of the second chromophorous compound (34) in said sample (30);

determination, by optical measurement of the absorption characteristics of the chromophorous and fluorescent compound (33), of the content of the chromophorous and fluorescent compound (33) in said sample (30), said determination comprising the following operations:

emission, by second means of emission (13, 14) towards said sample (30), of a third (131) and of a fourth (141) optical radiation, of different wavelengths, such that one of the third and fourth radiations is absorbed by the chromophorous and fluorescent compound and the other is only slightly or not at all absorbed by the chromophorous and fluorescent compound, measurement, by second measurement means, of at least one unabsorbed part of the third and fourth radiations (131, 141), and determination, from said second measurement, of the content of the chromophorous and fluorescent compound (33) in said sample (30), characterized in that said first measurement means and said second measurement means comprise shared detection means (21), said method also comprising at least one first filtering, between said sample (30) and the detection means, (21), said filtering being intended to:

block said first and second radiations (111, 121) from passing through to said detection means, (21), allow, at least partly, the unabsorbed part of said third and fourth radiations (131, 141) to pass through to said detection means, (21), and allow, at least partly, said radiations of fluorescence (112, 122) induced by said first and second radiations (112, 121) to pass through.

2. The method according to claim 1, wherein the first radiation (iii) is chosen such that its wavelength:
is not comprised within an absorption wavelength band of said second chromophorous compound (34), and
is comprised within an excitation wavelength band of the fluorescence of the chromophorous and fluorescent compound (33); and the second radiation (121) is chosen such that its wavelength:
is comprised within an absorption wavelength band of said second chromophorous compound (34), and
is comprised within an excitation wavelength band of the fluorescence of the chromophorous and fluorescent compound (33).

3. The method according to claim 1, wherein the third radiation (131) is chosen such that its wavelength:
1. is comprised within an absorption wavelength band of said chromophorous and fluorescent compound (33), and
2. is not comprised in an absorption wavelength band of the second chromophorous compound (34); and the fourth radiation (141) is chosen such that its wavelength:
3. is not comprised in an absorption wavelength band of the chromophorous and fluorescent compound (33), and
4. is not comprised within an absorption wavelength band of the second chromophorous compound (34).

4. The method according to claim 1, wherein said method comprises, between the emission means (11-14) and the sample (30), a second optical filtering provided to block part of the radiations (11-14) emitted towards said sample (30).

5. The method according to claim 1, wherein the second optical radiation (121) is emitted at a predetermined intensity and the first optical radiation (111) is emitted at a variable intensity so that the radiations of fluorescence (112, 122) induced by each of said first and second radiations (iii, 121) are equal in intensity.

6. The method according to claim 1, wherein the intensity of the first radiation (iii) is adjusted as a function of a control signal (So), in relation to the radiations of fluorescences (112, 122) induced by said first radiation (iii) and by the second radiation (121).

7. The method according to claim 1, wherein the intensities of the first, second, third and fourth radiations (iii, 121) vary alternately, with a phase shift, at a predetermined frequency.

8. The method according to claim 1, further comprising a step of determination of a quantity proportional to the ratio between the content of chromophorous and fluorescent compound (33) and the content of second chromophorous compound (34).

9. A method for characterizing a plant leaf, comprising following the method for characterizing a sample of biological tissue (30) of claim 1, wherein the biological tissue (30) is the plant leaf, the chromophorous and fluorescent compound (33) is chlorophyll and the second chromophorous compound (34) comprises a compound of the family of the polyphenols or the phenylpropanoids.

10. The method according to claim 9, wherein,
the first radiation (111) has a wavelength chosen around 650 nm;
the second radiation (121) has a wavelength chosen around 370 nm;
the third radiation (131) has a wavelength chosen around 720 nm; and
the fourth radiation (141) has a wavelength chosen around 780 nm.

11. The method according to claim 9, wherein further comprising a determination of the nitrogen requirement of the plant as a function of the content of chlorophyll and polyphenols.

12. The method according to claim 10, wherein further comprising a determination of the nitrogen requirement of the plant as a function of the content of chlorophyll and polyphenols.

* * * * *